United States Patent [19]
Kronberg

[11] Patent Number: 5,217,009
[45] Date of Patent: Jun. 8, 1993

[54] COMPACT BIOMEDICAL PULSED SIGNAL GENERATOR FOR BONE TISSUE STIMULATION

[76] Inventor: James W. Kronberg, 108 Independent Blvd., Aiken, S.C. 29801

[21] Appl. No.: 727,705

[22] Filed: Jul. 10, 1991

[51] Int. Cl.$^5$ .............................................. A61N 1/36
[52] U.S. Cl. ................... 128/419 F; 128/421; 128/422
[58] Field of Search ............... 128/421, 419 F, 422, 128/82.1

[56] References Cited

U.S. PATENT DOCUMENTS

| | | | |
|---|---|---|---|
| 3,540,453 | 11/1970 | Sugimori | 128/422 |
| 4,249,537 | 2/1981 | Lee et al. | 128/422 |
| 4,408,608 | 10/1983 | Daly et al. | 128/421 |
| 4,414,979 | 11/1983 | Hirshorn et al. | 128/419 |
| 4,533,988 | 8/1985 | Daly et al. | 363/127 |
| 4,548,208 | 10/1985 | Niemi | 128/419 |
| 4,592,359 | 5/1986 | Galbraith | 128/419 |
| 4,602,638 | 7/1986 | Adams | 128/419 F |
| 4,672,951 | 6/1987 | Welch | 128/1.5 |
| 5,103,806 | 5/1992 | McLeod et al. | 128/419 F |
| 5,107,835 | 4/1992 | Thomas | 128/422 |
| 5,109,848 | 5/1992 | Thomas et al. | 128/421 |

FOREIGN PATENT DOCUMENTS 3904304 8/1990 Fed. Rep. of Germany ... 128/419 F

OTHER PUBLICATIONS

Levy, "Induced Osteogenesis by Electrical Stim.," J. Electrochem. Soc.:Electrochemical Science, Sep. 1971.

Primary Examiner—Kyle L. Howell
Assistant Examiner—Kennedy J. Schaetzle
Attorney, Agent, or Firm—Harold M. Dixon; William R. Moser; Richard E. Constant

[57] ABSTRACT

An apparatus for stimulating bone tissue for stimulating bone growth or treating osteoporosis by applying directly to the skin of the patient an alternating current electrical signal comprising wave forms known to simulate the piezoelectric constituents in bone. The apparatus may, by moving a switch, stimulate bone growth or treat osteoporosis, as desired. Based on low-power CMOS technology and enclosed in a moisture-resistant case shaped to fit comfortably, two astable multivibrators produce the desired waveforms. The amplitude, pulse width and pulse frequency, and the subpulse width and subpulse frequency of the waveforms are adjustable. The apparatus, preferably powered by a standard 9-volt battery, includes signal amplitude sensors and warning signals indicate an output is being produced and the battery needs to be replaced.

18 Claims, 1 Drawing Sheet

COMPACT BIOMEDICAL PULSED SIGNAL GENERATOR FOR BONE TISSUE STIMULATION

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to an apparatus and method for the electrical treatment of biological tissue. In particular, the present invention relates to an apparatus and method for providing a series of pulses for electrical stimulation of bone growth.

2. Discussion of Background

Human bone is a combination of organic and mineral components. The chief mineral constituent of bone is hydroxyapatite, a complex calcium phosphate ($Ca_5(PO_4)_3OH$) in crystalline form. Hydroxyapatite is piezoelectric: that is, it generates an electric charge or current when mechanically stressed. These electric signals are detected by nearby bone cells, stimulating them to deposit increased amounts of hydroxyapatite in response to the stress. This appears to be part of a biological feedback mechanism causing bone to be strengthened automatically at points of stress concentration. This mechanism also controls fracture healing. A similar feedback mechanism appears to control the mineral content of intact bone. When this mechanism breaks down, osteoporosis can result. In the case of a bone fracture, the normal healing process stops, resulting in a nonunion. Conventional treatment of nonunions usually involves surgical procedures, for example, "freshening" the broken ends of the bone or inserting pins to align the fracture. Surgery is, in effect, a new injury which restarts the dormant healing process. In many cases, however, conventional treatment is unsuccessful.

The weak electrical signals generated by bone were extensively studied and analyzed during the 1960's. During the 1970's, the results of these basic studies were applied in stimulating the healing of intractable nonunions and congenital pseudarthroses, with success rates of about 75%-80%. These results are not affected by factors such as infection, number of prior operative procedures, or soft-tissue or nerve defects. Other beneficial effects have been observed in the healing of soft-tissue injuries, including the healing of chronic skin wounds and the recovery of feeling in chronically numb skin grafts.

A waveform used for stimulation of bone growth is shown in FIG. 1. A series of pulses 10 consists of pulses 12, with pulse width 14 (5 msec), amplitude 16, and pulse interval 18 (61 msec) for a frequency of about 15 Hz. Each pulse 12 contains subpulses 20 with subpulse width 22 (200 μsec) and subpulse interval 24 (28 μsec) for a frequency of about 440 Hz. A waveform used for treatment of osteoporosis, shown in FIG. 2, consists of a series of pulses 30, with pulses 32 of pulse width 34 (380 μsec), amplitude 36, and pulse interval 38 (13.5 msec) for a frequency of about 72 Hz. AC signals such as these, at levels comparable to normal piezoelectric signals (about 1 millivolt per centimeter) can increase the normal rate of bone healing and, more importantly, can stimulate healing in nonunions. AC signals several orders of magnitude more powerful have virtually the same effect as the weaker signals, indicating that a threshold effect is involved. DC signals, on the other hand, can damage soft tissues, and, if too strong, can lead to bone necrosis instead of healing.

Invasive techniques necessitate the implantation of electrodes below the skin (typically at the site of a nonunion), requiring surgery. See Adams (U.S. Pat. No. 4,602,638), and Hirshorn et al. (U.S. Pat. No. 4,414,979). Besides carrying some danger of infection, such procedures cause additional patient stress and require continuing professional care.

Much of the recent work in electrical bone growth stimulation has focused on noninvasive techniques using induced electric fields. The field generator and the patient are coupled by means of induction coils. See Welch (U.S. Pat. No. 4,672,951), and Niemi (U.S. Pat. No. 4,548,208). The coils are placed around the area to be treated, such as against the patient's skin or a plaster cast. Radio-frequency (RF) signals applied to the coils induce signals of similar form in bone and other tissues. This method is noninvasive, thereby simplifying patient care. Only AC signals are transmitted while DC is wholly blocked. However, such coupling is very inefficient at the low frequencies used. Elaborate circuitry is needed to drive the coils with a deliberately distorted waveform, or a waveform modulated with higher frequencies, so that the currents induced within the bone will approximate natural piezoelectric signals. Alternatively, simplicity is retained at the cost of added power drain by using different types of signals such as sine waves.

Coils, high-frequency generators, and modulating and driving circuitry all add to the weight, bulk, cost and power requirements of the signal generator. Generators presently in use may cost several thousand dollars each. Nominally portable equipment is driven by heavy, rechargeable battery packs with limited capacity; stationary devices may require connection to AC power. The inconvenience of using existing stimulators mandates intermittent use by patients, typically for only three to eight hours per day. Some models include circuitry to monitor use and help ensure patient compliance, which adds to the cost of the equipment. Often, coils must be custom-made for the individual patient. The signal generators must then be adjusted for optimum field distribution and adequate signal penetration into the bone. This also adds to the cost and may delay the beginning of treatment.

An ideal signal generator for the electrical stimulation of bone growth would be lightweight, compact, fully self-contained, inexpensive to build and maintain, safe for unsupervised home use, and require no external coils or battery pack. Such a stimulator could be taped directly to an arm or leg cast without adding significant weight or bulk. The stimulator would produce pulsed electric signals such as those shown in FIGS. 1 and 2 for treatment of fractures or osteoporosis, respectively or such other tissue treatment as may be desired. Signals would be delivered efficiently and uniformly throughout the treatment area, in a manner producing little or no distortion. No special traning would be required for use. Treatment would be continuous, minimizing problems of patient compliance. The stimulator would operate at low power levels, so there would be no shock hazard even in case of malfunction. Power would preferably be furnished by readily-available and inexpensive radio batteries.

No bone-growth stimulator presently available, or known to have been described in the medical literature, offers this combination of advantages.

SUMMARY OF THE INVENTION

According to its major aspects and broadly stated, the present invention is a compact signal generator that operates at low power and produces adjustable pulsed signals in the frequency ranges of interest for electrical stimulation of bone growth and osteoporosis treatment. The signal generator applies the signals to the skin of the patient using skin-contact electrodes. The signal generator incorporates complementary metal oxide semiconductor (CMOS) integrated timing circuits connected as astable multivibrators to produce pulsed signals. Pulse and subpulse durations are adjustable by means of variable resistors or some other convenient means. If desired, the output signal amplitude can be controlled by a potentiometer or otherwise. Power is supplied by a standard 9-volt battery, or some other similar power source such as a rechargeable battery or power supply for use with AC line current. The signal generator circuitry is mounted on a circuit board with battery snaps at one end and output terminals for connection to the patient-contact electrodes at the other end. The signal generator is in a case having one flat or slightly concave side, an opposing convex side, and all edges rounded. The circuit board and battery are slidably contained within the case to facilitate easy access to replace the battery. An indicator light is provided for monitoring circuit functioning.

An important feature of the present invention is the use of CMOS integrated timing circuits in astable multivibrator circuits to produce the pulsed signals. CMOS circuits result in a low-maintenance device and circuits having minimal power requirements. Therefore, inexpensive low-voltage batteries can be used as the power source and are preferred therefor. Such batteries would last approximately one week during use. Furthermore, the signal generator does not produce high internal voltages or frequencies likely to induce atrial fibrillation since the signal generator is not connected to commercial AC power lines and does not produce high voltages internally. Thus, the apparatus is suitable for home use.

Another feature of the present invention is the provision for adjusting the pulse and subpulse duration and frequency by means of variable resistors or some other convenient means. If desired, the output signal amplitude can also be adjusted by a potentiometer or otherwise. This feature allows the apparatus to be optimized for bone tissue stimulation or adjusted for stimulation of other cellular tissue.

Yet another feature of the present invention is the small size, light weight and shape of the encased circuit components. The components may be encapsulated in resin for protection from moisture, mechanical damage, or accidental disconnection of the power source. The outer case preferably has one flat or slightly concave side, the opposite side convex, and all edges rounded to facilitate attachment to the outside of a cast and reduce the likelihood of snagging on objects or clothing while in use.

Still another feature of the present invention is the use of skincontact electrodes such as electrocardiogram electrodes. Low-frequency AC signals, simulating natural piezoelectric signals, thereby pass without distortion directly from the signal generator to the patient's body through the skin. Such electrodes might be incorporated in a cast, slipped into its ends, attached to the patient's skin, or otherwise placed in the desired treatment configuration.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

The present invention is a low-power, compact, lightweight signal generator for the electrical stimulation of bone growth or osteoporosis treatment, transmitting the signal using skin-contact electrodes such as electrocardiogram electrodes. The signal generator is powered by inexpensive low-voltage batteries which need replacement approximately once per week.

Because of the threshold effect, low-level signals are as effective as high-level ones in stimulating bone growth. Low-level AC signals with direct-contact skin electrodes will not cause electrolytic damage, since only small currents pass through the skin's electrical resistance. Such electrodes, for example, could be the type used in taking electrocardiograms. Direct connection to the skin permits low-frequency signals simulating natural piezoelectric signals to pass without distortion from the signal generator through the skin to the bone tissue in the patient. Thus, no high-frequency modulation or deliberate counter-distortion is needed. This greatly reduces the size, weight, complexity and expense of the circuitry needed.

New CMOS integrated timing circuits have recently become available. Such CMOS circuits require minimal power, a feature which is important for low-maintenance devices for medical use. The description below applies to a signal generator incorporating CMOS technology and capable of generating signals of the types shown in FIGS. 1 and 2. It will be obvious to those skilled in the art, however, that similar results could be obtained by substituting other circuit components in addition to the specific ones described.

Figure 3:
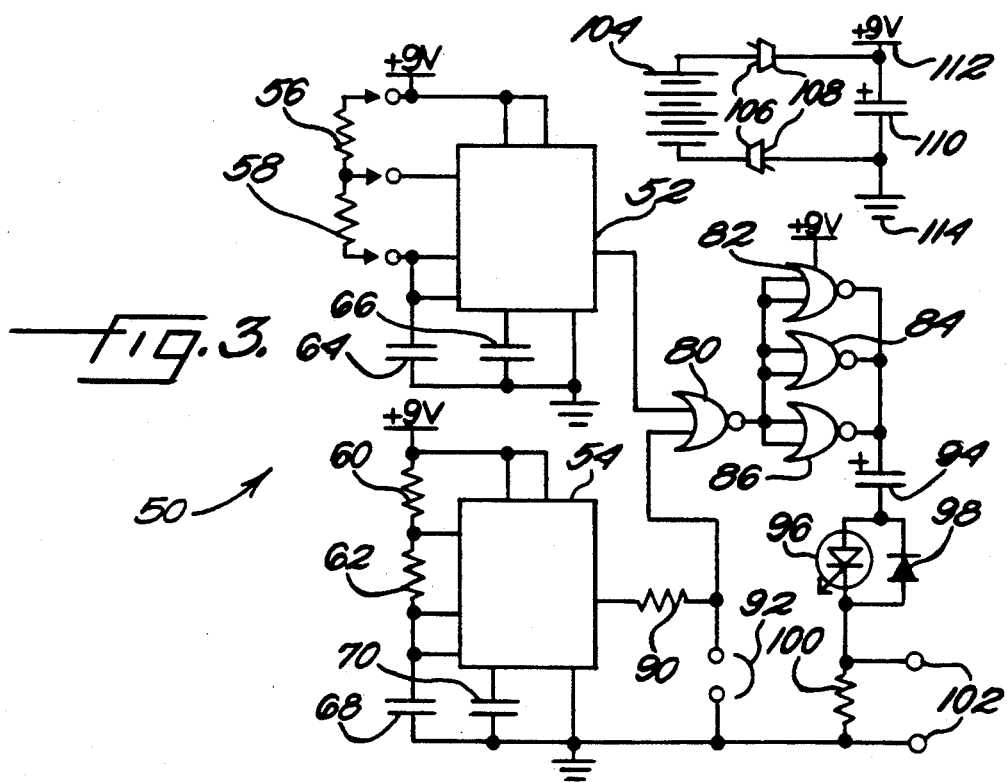
FIG. 3 is an electrical schematic diagram of a pulsed signal generator according to a preferred embodiment of the present invention.

One preferred embodiment of the present invention is shown in FIG. 3. Circuit 50 includes two CMOS integrated timing circuits 52 and 54, preferably Texas Instruments TLC-555 or equivalent devices. Devices 52 and 54, four resistors 56, 58, 60 and 62, and four capacitors 64, 66, 68 and 70, form the timing circuitry. Devices 52 and 54 are connected as astable multivibrators. When so connected, the TLC-555 produces a series of rectangular pulses with "high" and "low" voltages roughly equal to the supply voltages and with pulse durations given by the following equations:

$$T_{high} = 0.693(R_1 + R_2) \times C \quad T_{low} = 0.693 R_2 \times C$$

For device 52, $R_1$ is resistor 56, $R_2$ is resistor 58, and C is capacitor 64; for device 54 these are resistor 60, resistor 62 and capacitor 68 respectively. Capacitors 66 and 70 may be of any convenient value greater than about 0.001 μfarad. Preferred values for the other six components are:

| Resistor 56 | 750KΩ for stimulation of bone growth; 180KΩ for treatment of osteoporosis |
|---|---|
| Resistor 58 | 68KΩ for stimulation of bone growth; 5.6KΩ for treatment of osteoporosis |
| Resistor 60 | 110KΩ |
| Resistor 62 | 18KΩ |
| Capacitor 64 | 0.1 μfarad |
| Capacitors 66, 68, 70 | 0.0022 μfarad |

Figure 1:
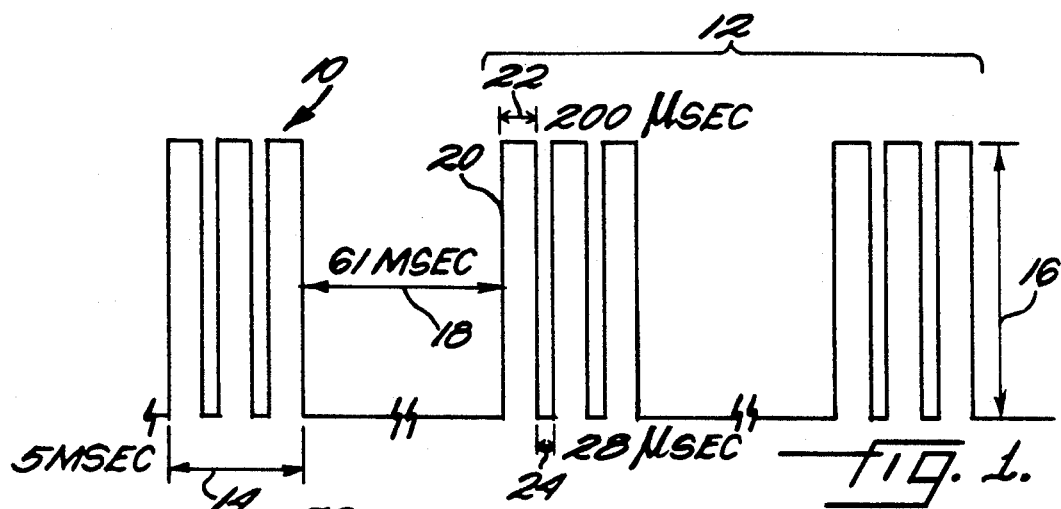
FIG. 1 is a waveform used for stimulation of bone growth.
Figure 2:
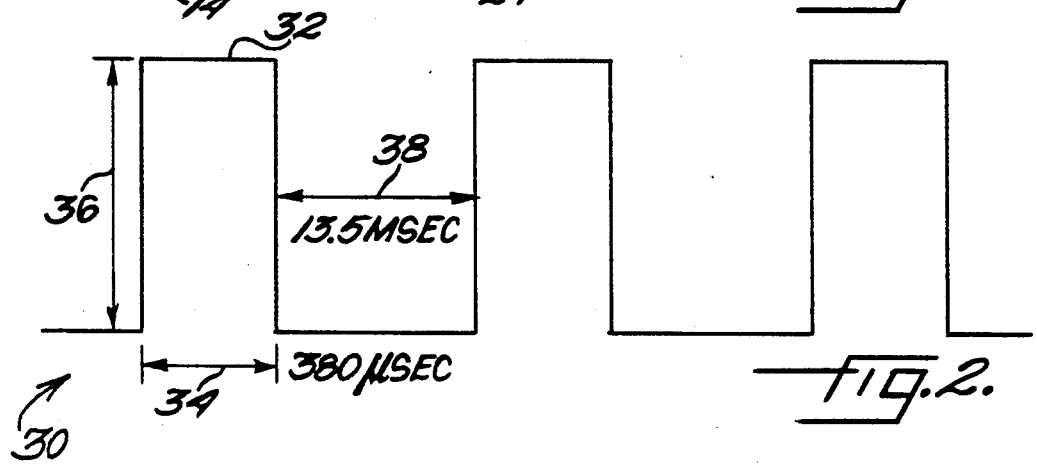
FIG. 2 is a waveform used for treatment of osteoporosis.

"High" and "low" pulse durations obtained with these values are substantially those shown in FIGS. 1 and 2. For stimulation of bone growth, device 52 generates the low frequency pulses 12 and device 54 the higher frequency subpulses 20 of pulse train 10 (FIG. 1). For osteoporosis treatment, device 54 is deselected, and the output is as shown in FIG. 2. Resistors 56 and 58 may be variable within the desired range, for example, resistor 56 could cover the range 100 KΩ-1,000 KΩ and resistor 58 could vary within the range 1 KΩ-100 KΩ. Alternatively, resistors 56 and 58 may be mounted on a plug-in module, with different modules having different resistance values for stimulation of bone growth or for osteoporosis treatment. If desired, resistors with the appropriate fixed values might be incorporated into circuit 50, with the desired combination selected by a switch or some other convenient means. Other variations can be made within the scope of the present invention.

Outputs from devices 52 and 54 are combined by CMOS NOR gate 80, then amplified by the parallel combination of gates 82, 84, and 86. These are preferably the four gates contained in an MC14001B or equivalent CMOS quad NOR-gate package. Resistor 90 (preferably about 100 KΩ) and jumper 92 permit the substitution of ground potential for the output of device 54, thus effectively deselecting device 54, yielding continuous 380-μsecond pulses for osteoporosis treatment. Alternatively, a switch or other signal-substitution means could be used, or the output could be taken directly from device 52 without passing through additional circuitry.

The amplified output from gates 82, 84 and 86 consists of a series of intermittent rectangular pulses having a significant DC component. Capacitor 94, preferably a one-μfarad tantalum electrolytic type, blocks the DC portion of the output signal. The AC portion of the output signal then passes through the combination of light-emitting diode 96 and steering diode 98, which give a visible indication of circuit functioning and battery condition. Diodes 96 and 98 are not essential to circuit functioning and may be omitted if convenient.

Current passing through capacitor 94 and diodes 96 and 98 develops an AC voltage across resistor 100, which is preferably about 470 Ω. Resistor 100 provides a path to ground for any small DC current which may leak through the capacitor. If diodes 96 and 98 are not used, resistor 100 may be as large as 10KΩ. If desired, resistor 100 can be replaced by a potentiometer so that an adjustable fraction of the output voltage, rather that its full value, may be applied across output terminals 102. This may be desirable, for example, in the treatment of fractures in small bones such as finger bones, or treatment of children.

Circuit 50 is powered by a common, rectangular 9-volt carbonzinc or alkaline "radio" battery 104 whose snap terminals 106 mate with corresponding snaps 108 on circuit 50. To prevent power surges which could damage the CMOS components, a 5-10-μfarad tantalum electrolytic capacitor 110 is connected across terminals 112 and 114. Circuit 50 normally operates continuously until the battery is exhausted and needs replacement. With an average drain of about 0.7 milliampere, a typical battery will last for about a week. Capacitor terminals 112 and 114 connect with all positive (+9 V) and all negative (ground) supply pins, respectively, in the circuit. Alternatively, some other power source such as a rechargeable battery or power supply for use with AC line current may be used.

The circuit components are mounted on a circuit board measuring about 2.5×5.0 centimeters, with battery snaps 108 at one end and output terminals 102, for connection to the patient-contact electrodes, at the other. The components are laid out on the board as may be convenient. The shorter side of the board corresponds to the width of a standard 9-volt rectangular battery. When assembled, the signal generator (excluding electrodes and electrode leads) measures about 1.7×2.5×9.5 centimeters.

The circuit components may be encapsulated in resin or some other means of protection from moisture, mechanical damage, or accidental disconnection of the battery. The signal generator preferably includes an outer case, which may have one flat or slightly concave side, the opposite side convex, and all edges smoothly rounded. This configuration facilitates taping the signal generator to the outside of an arm or leg cast and reduces the likelihood of its snagging on objects or clothing while in use. To facilitate easy access to the battery for replacement, the circuit board and battery may be slidably contained within the case. LED 96, if used, may be exposed, or visible through a transparent area on the case for ease in monitoring circuit functioning. Output terminals 102 could be small sockets or other connection means, so that standard electrocardiogram-type electrodes could be readily attached. Such electrodes might be incorporated in the cast, slipped into its ends, or attached to the patient's skin, or otherwise placed in a convenient treatment configuration.

It will be apparent to those skilled in the art that many changes and substitutions can be made to the preferred embodiment herein described without departing from the spirit and scope of the present invention which is defined by the appended claims.

What is claimed is:

1. An apparatus for generating an electrical signal for stimulating biological tissue within a patient's skin, said apparatus comprising:

first circuit means for generating a first series of electrical pulses, each pulse having a first amplitude, a first width and a first frequency, said first width and said first frequency selected to stimulate bone tissue;

second circuit means for generating a second series of electrical pulses, each pulse having a second amplitude, a second width and a second frequency, said second width and said second frequency selected to stimulate bone tissue, said second amplitude being equal to said first amplitude;

means for combining said first series and said second series into a combined signal;

means for eliminating any direct current component of said combined signal to produce an alternating current signal; and contact electrodes for applying said alternating current signal received from said eliminating means to said tissue through said skin, said electrodes adapted to be attached to said skin.

2. The apparatus of claim 1, wherein said first width is in the range 0.1-10 msec, said first frequency is in the range 5-25 Hz, said second width is in the range of 100-300 μsec and said second frequency is in the range 100-1000 Hz.

3. The apparatus of claim 1, further comprising switch means for selecting and deselecting said second circuit means so that, when said switch means is selected, said combining means combines said first and second series into said combined signal and, when said switch means is deselected, said second series is deselected.

4. The apparatus of claim 1, further comprising means for adjusting the amplitude of said combined signal.

5. The apparatus of claim 1, further comprising means for varying said first width and said first frequency, and means for varying said second width and said second frequency.

6. The apparatus of claim 1, further comprising:
means for selecting a preferred combined signal amplitude,
means for sensing the amplitude of said combined signal; and
means for producing a warning signal if said amplitude is less than said preferred amplitude.

7. The apparatus of claim 1, further comprising:
means for deselecting said second circuit means;
means for adjusting the amplitude of said combined signal;
means for varying said first width and said first frequency;
means for varying said second width and said second frequency;
means for selecting a preferred combined signal amplitude,
means for sensing the amplitude of said combined signal; and
means for producing a warning signal if said amplitude is less than said preferred amplitude.

8. An apparatus for generating an electric signal for stimulating bone tissue within the skin of a patient, said apparatus comprising:
a first stable multivibrator circuit for generating a first series of electrical pulses, each pulse having a first amplitude, a first width and a first frequency, said first width and said first frequency selected to stimulate bone tissue;
a second stable multivibrator circuit for generating a second series of electrical pulses, each pulse having a second amplitude, a second width and a second frequency, said second width and said second frequency selected to stimulate bone tissue, said second amplitude being equal to said first amplitude;
means for combining and amplifying said first series and said second series into a combined signal;
means for eliminating any DC component of said combined signal leaving an alternating current signal; and contact electrodes for applying said alternating current signal received from said eliminating means to said skin, said electrodes adapted to be attached to said skin.

9. The apparatus of claim 8, wherein said first width is in the range 0.1-10 msec, said first frequency is in the range 5-25 Hz, said second width is in the range of 100-300 μsec and said second frequency is in the range 100-1000 Hz.

10. The apparatus of claim 8, further comprising switch means for selecting and deselecting said second circuit means so that, when said switch means is selected, said combining means combines said first and second series into said combined signal and, when said switch means is deselected, said second series is deselected.

11. The apparatus of claim 8, further comprising means for adjusting the amplitude of said combined signal.

12. The apparatus of claim 8, further comprising:
means for selecting a preferred combined signal amplitude;
means for sensing the amplitude of said combined signal; and
means for producing a warning signal if said amplitude is less than said preferred amplitude.

13. The apparatus of claim 8, further comprising means for varying said first width and said first frequency, and means for varying said second width and said second frequency.

14. The apparatus of claim 8, further comprising:
means for deselecting said second astable multivibrator circuit;
means for adjusting the amplitude of said combined signal;
means for varying said first width and said first frequency;
means for varying said second width and said second frequency;
means for selecting a preferred combined signal amplitude,
means for sensing the amplitude of said combined signal; and
means for producing a warning signal if said amplitude is less than said preferred amplitude.

15. An apparatus for generating an electrical signal for stimulating bone growth and treating osteoporosis by stimulating bone tissue within the skin, said apparatus comprising:
a first astable multivibrator circuit having a CMOS integrated timing circuit for generating a first series of electrical pulses, each pulse having a first amplitude, a first width in the range 0.1-10 msec and a first frequency in the range 5-25 Hz;
a second astable multivibrator circuit having a CMOS integrated timing circuit for generating a second series of electrical pulses, each pulse having a second amplitude, a second width 100-300 μsec and a second frequency in the range 100-1000 Hz, said second amplitude being equal to said first amplitude;
switch means for selecting and deselecting said second astable multivibrator circuit so that, when said switch means is selected, said apparatus can stimulate bone growth but not treat osteoporosis and, when said switch means is deselected, said device treats osteoporosis but does not stimulate bone growth;

means for combining and amplifying said first series and said second series into a combined signal; and means for eliminating any DC component of said combined signal leaving an alternating current signal;

skin contacts for receiving said alternating current signal from said eliminating means and applying said alternating current to said skin.

16. The apparatus of claim 15, wherein said first width and said first frequency, and said second width and said second frequency, are selected to stimulate bone tissue.

17. The apparatus of claim 15, further comprising means for adjusting the amplitude of said combined signal.

18. The apparatus of claim 15, further comprising:

means for selecting a preferred combined signal amplitude;

means for sensing the amplitude of said combined signal; and means for producing a warning signal if said amplitude is less than said preferred amplitude.

* * * * *